United States Patent [19]

Kajimoto et al.

[11] Patent Number: 4,918,186

[45] Date of Patent: Apr. 17, 1990

[54] PROCESS FOR PRODUCING CYCLIC UREAS

[75] Inventors: Nobuyuki Kajimoto; Teruyuki Nagata; Masaru Wada, all of Fukuoka, Japan

[73] Assignee: Mitsui Toatsu Chemicals, Inc., Tokyo, Japan

[21] Appl. No.: 320,228

[22] Filed: Mar. 7, 1989

Related U.S. Application Data

[63] Continuation-in-part of Ser. No. 44,836, Apr. 30, 1987, abandoned.

[30] Foreign Application Priority Data

May 6, 1986 [JP] Japan .................... 61-101935
May 6, 1986 [JP] Japan .................... 61-101937

[51] Int. Cl.$^4$ ............ C07D 233/34; C07D 239/36; C07D 243/04
[52] U.S. Cl. ................. 540/492; 544/315; 548/317
[58] Field of Search ........ 548/317; 544/215; 540/492

[56] References Cited

U.S. PATENT DOCUMENTS 3,838,165  9/1974  Blochl .................... 544/315

FOREIGN PATENT DOCUMENTS 883902   7/1953  Fed. Rep. of Germany ...... 548/229
917972   9/1954  Fed. Rep. of Germany ...... 548/229
1126392  3/1962  Fed. Rep. of Germany ...... 548/313

OTHER PUBLICATIONS

Puschin et al., "Compounds of Phosgene, etc." (U.S. Patent and Trademark Office) (Jun. 1986).
Chemische Berichte, vol., 93, 1960, "Darstellung N-haltiger Heterocyclen uber silicium-organischs Verbindungen; eine neue Harnsaure-Synthese", Lecnhard Birkofer, Hans Peter Kuhlthau und Alfred Ritter. (Chemical Abstracts, vol. 55, 5484b).
Journal of Chemical Society, 1947, pp. 307-318, "Respiratory Stimulants. Part I. Fully-Substituted Ureas Derived From Alpha Omega-Alkylenediamines", W. R. Bcon.

Primary Examiner—Robert T. Bond
Attorney, Agent, or Firm—Jeffers, Hoffman & Niewyk

[57] ABSTRACT

A process for producing a cyclic urea is provided. The process comprises reacting a diamine expressed by the formula (II)

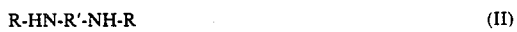

R-HN-R'-NH-R      (II)

wherein R represents hydrogen atom or a lower alkyl group and R' represent dimethylene group, a lower alkyl group-substituted dimethylene group, trimethylene group, a lower alkyl group-substituted trimethylene group, tetramethylene group, a lower alkyl group-substituted tetramethylene group, but a case where R represents hydrogen atom and R' represent dimethylene group, a case where R represents hydrogen atom and R' represents a lower alkyl group-substituted dimethylene group and a case where R represent methyl group and R' represents dimethylene group are excluded, with phosgene in the presence of a dehydrochlorinating agent. In the process, the diamine is first converted to its hydrochloride, followed by reacting the hydrochloride with phosgene in water solvent while maintaining a pH of the reaction liquid in the range of 5.0 to 8.0 by said dehydrochlorinating agent to obtain a cyclic urea expressed by the formula (I)

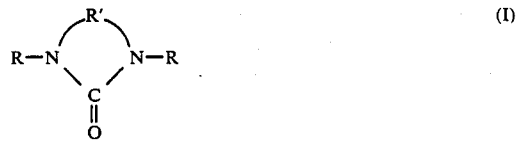

wherein R and R' are each as defined above.

1 Claim, No Drawings

PROCESS FOR PRODUCING CYCLIC UREAS

CROSS REFERENCE TO RELATED APPLICATIONS

This is a continuation-in-part of application Ser. No. 044,836 filed Apr. 30, 1987, now abandoned.

BACKGROUND OF THE INVENTION

1. Field of the Invention

This invention relates to a process for producing a cyclic urea by reacting a diamine with phosgene, which cyclic urea is expressed by the formula (I)

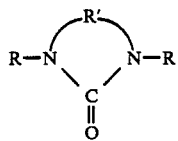
(I)

wherein R represents hydrogen atom or a lower alkyl group and R' represents dimethylene group, a lower alkyl group-substituted dimethylene group, trimethylene group, a lower alkyl group-substituted trimethylene group, tetramethylene group or a lower alkyl group-substituted tetramethylene group, but a case where R represents hydrogen atom and R' represents dimethylene group, a case where R represents hydrogen atom and R' represents a lower alkyl group-substituted dimethylene group and a case where R represents methyl group and R' represents dimethylene group are excluded.

Cyclic ureas of the formula (I) such as 2-imidazolidinones, tetrahydro-2(b 1H)-pyrimidines, hexahydro-2H-1,3-diazepin-2-ones, etc. are useful substances as non-protonic polar solvents and as an intermediate for pharmaceuticals, pesticides, etc. In particular, they are superior solvents for high-molecular compounds such as polyamides, polyvinyl chloride, polyvinyl alcohol, polystyrene, polyurethanes, phenol resins, etc. and also form complexes with many inorganic salts to dissolve therein and further are used as solvents for many organic reactions.

2. Description of the Prior Art

A process for obtaining 2-imidazolidinones by reacting diamines corresponding to 2-imidazolidinones of the above formula with phosgene has not yet been known, but a process for obtaining 1,3-dimethyl-2-imidazolidinone which is a similar compound to the above cyclic ureas of the formula (I), with a yield of 13% by reacting N,N'-dimethyl-1,2-ethanediamine with phosgene in toluene solvent has been known (J. Chem. Soc., 1947, page 315). However, the present inventors carried out the reaction of N,N'-dimethyl-1,2-propanediamine with phosgene in toluene solvent according to the above process, but the yield of 1,3,4-trimethyl-2-imidazolidinone belonging to the cyclic ureas of the formula (I) was less than 20%.

Further, as the process for producing the above tetrahydro-2(1H)-pyrimidinones, a process of reacting N,N'-dimethyl-1, 3-propanediamine with phosgene in toluene (J. Chem. Soc. page 315, 1947) and a process of reacting N,N'-bis (trimethylsilyl)-1,3-propanediamine with phosgene, followed by hydrolyzing the resulting tetrahydro-1,3-bis(trimethylsilyl)- 2(1H)-pyrimidinone (Chem. Ber. Vol. 93, page 2813, 1960) have been known.

However, as to the process of reacting N,N'-diamino-1,3propanediamine with phosgene in toluene, the present inventors followed the process, but the yield was less than 20%. Still further, according to the process of reacting N,N'-bis (trimethylsilyl)-1,3-propanediamine with phosgene, while the yield was 75%, it is necessary to obtain a silylating material so that the process is also not a process which can be carried out by directly reacting phosgene and also it is necessary to use an expensive silylating agent.

Further, as a process for producing the above-mentioned hexahydro-2H-1,3-diazepin-2-ones, a process of obtaining hexahydro-2H-1,3-diazepin-2-ones by directly reacting 1,4-butanediamines with phosgene has not yet been known, but as an indirect process, a process of reacting N,N'-bis(trimethylsilyl)-1,4-butanediamine with phosgene and then hydrolyzing the resulting hexahydro-1,3-bis(trimethylsilyl)-2H-1,3-diazepin-2-one (Chem. Ber. Vol. 93, page 2813, 1960) has been known.

However, according to this process, it is necessary to obtain the silylated compound of 1,4-butanediamine in advance using an expensive silylating agent, and also the yield of the reaction of the diamine with phosgene (such a reaction with phosgene will be hereinafter referred to as "phosgenation reaction") is as low as 60% ; hence the process has not been commercially satisfactory.

SUMMARY OF THE INVENTION

The object of the present invention is to provide a process for producing a cyclic urea of the formula (I) by converting diamine to its hydrochloride, and thereafter reacting the hydrochloride with phosgene, with a high yield and at a commercially low cost.

The present inventors have made extensive research on a commercial production process of a cyclic urea of the formula (I) from a diamine and phosgene, and as a result have found the following facts:

It is known that usually processes using phosgene are carried out under a condition of absence of water to the utmost and also phosgene is easily hydrolyzed in an alkaline aqueous solution; thus the reaction of diamines with phosgene has been expected to require a large excess of phosgene. Surprisingly enough, however, it has been found that in the reaction of the above-mentioned diamines of the present invention with phosgene, 1.0 to 1.5 times the theoretical quantity of phosgene is sufficient. Further, it has also been found that the yield of the objective product cyclic urea of the formula (I) is greatly improved in the presence of water solvent and a dehydrochlorinating agent as compared with those of the prior art. Still further it has been found that in the above case, when the pH at the time of the reaction is kept within a definite range i.e. 3.0 to 10.0 by the dehydrochlorinating agent in the presence of water, the yield is further improved.

The present invention resides in a process for producing a cyclic urea which comprises converting a diamine expressed by the formula (II)

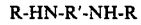 R-HN-R'-NH-R (II)

wherein R and R' are each as defined above into its hydrochloride, followed by reacting the hydrochloride with phosgene in the presence of water and a dehydrochlorinating agent to obtain a cyclic urea expressed by the formula (I)

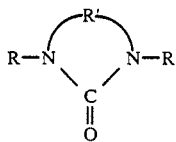

wherein R and R' are each as defined above.

DESCRIPTION OF THE PREFERRED EMBODIMENT

According to the present invention, since the reaction is carried out in a state where water is substantially present, that is, in water solvent, the hydrochloride of the diamine of the formula (II) successively formed by hydrochloric acid byproduced by the phosgenation reaction is not deposited at the time of the reaction, but it is dissolved in water so that the reaction can be carried out in a uniform state. Thus, it is possible to very easily control the pH at the time of the reaction.

Further, since a dehydrochlorinating agent is simultaneously used at the time of the reaction, the dehydrochlorinating agent not only functions effectively for catching byproduced hydrochloric acid, but also when the reaction is carried out while the pH is kept in the range of 3.0 to 10.0, the objective product is obtained with a high yield which is unexpected from the prior art. The reason is that when a monocarbamyl chloride initially formed by the phosgenation reaction of the diamines is intermolecularly cyclized, it has become possible to inhibit formation of byproducts formed by the intermolecular reaction and byproducts of dicarbamyl chlorides of diamines, etc. through pH control.

In the present invention, examples of the lower alkyl groups as defined for R and R' in the formula (II) are methyl, ethyl, propyl, butyl, etc. In the diamines of the formula (II) excluding, in the definitions thereof, a case wherein R represents hydrogen atom and R' represents dimethylene group, a case wherein R represents hydrogen atom and R' represents a lower alkyl group-substituted dimethylene group and a case wherein R represents methyl group and R' represents dimethylene group, concrete examples of the diamines are N,N'-diethylethylenediamine, N,N'-dipropyl-ethylenediamine, N,N'-dibutylethylenediamine, N,N'-dimethyl-1,2-propanediamine, N,N'-2- trimethyl-2, 3-butanediamine, N,N'-diethyl-1,2-propanediamine, etc. and these amines may be easily obtained from the corresponding alkyhalides and the corresponding alkylamines.

In the present invention, using these diamines as a raw material, the corresponding 2-imidazolidinones expressed by the formula (I) such as 1,3-diethyl-2-imidazolidinone, 1,3-dipropyl-imidazolidinones, 1,3-dibutyl-2-imidazolidinone, 1,3,4-trimethyl-2-imidazolidinone, 1,3,4,4,5-pentamethyl-2-imidazolidinone, 1,3-diethyl-4-methyl-2-imidazolidinone, etc. are obtained.

Further, concrete examples of diamines of the formula (II) wherein R represents a hydrogen atom and R' represents trimethylene group or a lower alkyl group-substituted trimethylene group are 1,3-propanediamine, N,N'-dimethyl-1,3-propanediamine, N,N'-diethyl-1,3-propanediamine, N,N'-dipropyl-1,3-propanediamine, N,N'-bis(1-methylethyl)-1,3-propanediamine, N,N'-dibutyl-1,3-propanediamine, 2,2-dimethyl-1,3-propanediamine, N,N',2,2-tetramethyl-1,3-propanediamine, etc. These 1,3-propanediamines may be easily obtained by reaction of 1,3-dihalopropanes with ammonia or the corresponding monoalkylamines or the like reaction.

In the present invention, using these amines as a raw material, it is possible to obtain the corresponding cyclic ureas of the formula (I) such as tetrahydro-2(1H)-pyrimidinone, tetrahydro-1,3-dimethyl-2(1H)-pyrimidinone, 1,3-diethyl- tetrahydro-2(1H)-pyrimidinone, tetrahydro-1,3-dipropyl-2(1H)-pyrimidinone, tetrahydro-1,3-bis(1-methylethyl)-2(1H)-pyrimidinone, 1,3-dibutyl-tetrahydro-2(1H)-pyrimidinone, tetrahydro-5,5-dimethyl-2(1H)-pyrimidinone, tetrahydro-1,3,5,5-tetramethyl-2(1H)-pyrimidinone, etc.

Further, concrete examples of diamines of the formula (II) wherein R represents hydrogen atom or a lower alkyl group and R' represents tetramethylene group or a lower alkyl group-substituted tetramethylene group are 1,4-butanediamine, N,N'-dimethyl-1,4-butanediamine, N,N'-diethyl-1,4-butanediamine, N,N'-dipropyl-1,4-butanediamine, N,N'-dibutyl-1,4-butanediamine, 2,5-dimethyl-2,5-hexanediamine, etc. These 1,4-butanediamines may be easily obtained by reaction of 1,4-dihalobutanes and ammonia or the corresponding monoalkylamines or the like reaction.

In the present invention, using these diamines as a raw material, it is possible to obtain the corresponding cyclic ureas expressed by the formula (I) such as hexahydro-2H-1,3-diazepin-2-one, hexahydro-1,3-dimethyl-2H-1,3-diazepin-2-one, 1,3-diethylhexahydro-2H-1,3-diazepin-2-one, hexahydro-1,3-dipropyl-2H-1,3-diazepin-2-one, hexahydro-1,3-dibutyl-2H-1,3-diazepin-2-one, hexahydro-4,4,7,7-tetramethyl-2H-1,3-diazepin-2-one, etc.

In the present invention, the diamines are first converted into their hydrochlorides followed by reacting them with phosgene. In the process of carrying out the reaction while keeping the pH within a range of 3.0–10.0, it is advantageous to feed the diamines in the form of their hydrochlorides from the beginning of the reaction.

When the diamines are used in the form of their hydrochlorides, if hydrochloric acid is used in an equivalent quantity and the resulting diamine dihydrochlorides are fed, the pH at the beginning of the reaction is about 3 and even if the resulting dihydrochlorides are phosgenated, the reaction rate is very low.

Thus, when the amines are used in the form of their hydrochlorides, it is preferred to react these in the form close to monohydrochlorides obtained by reacting hydrochloric acid in a quantity less than equivalent, and if the dihydrochlorides are fed from the beginning, it is preferred to carry out dehydrochlorination in advance with the dehydrochlorinating agent to make the pH 3 or more, followed by phosgenation reaction.

Further, if the diamines are fed as they are and reacted, the pH at the beginning of the reaction becomes 11 or more; thus it is preferred to add hydrochloric acid in advance of the phosgenation reaction to make the pH 10 or less, followed by the reaction.

Water is used as the solvent in the present invention. It may be placed in the reactor in advance or introduced together with the dehydrochlorinating agent, e.g. dropwise introduced in the form of an aqueous solution of an alkali metal compound. The quantity of water used has no particular limitation, but a quantity enough to keep a uniform reaction is preferred and 0.5 to 50 times by weight, preferably 3 to 30 times by weight the weight of the diamines.

Preferable examples of the dehydrochlorinating agent used in the present invention are alkali metal compounds such as NaOH, KOH, $Na_2CO_3$, $K_2CO_3$, etc. or tertiary amines such as aliphatic tertiary amines, e.g. trimethylamine, triethylamine, etc., aromatic tertiary amines e.g. dimethylaniline, diethylaniline, etc., and heterocyclic tertiary amines e.g. pyridine, methylpyridine, pyradine, etc. If no dehydrochlorinating agent is used, the raw material itself becomes an agent for catching byproduced hydrochloric acid so that it is difficult to further advance the reaction. The reaction temperature in the present invention has no particular limitation, but it is preferred to carry out the reaction at a temperature in the range of 0°–70° C.

The quantity of the dehydrochlorinating agent used in the present invention varies depending on the pH range at the time of the reaction, and for example if the reaction is carried out in a pH range close to neutrality, the quantity is suitably determined so as to correspond to the quantity of byproduced hydrochloric acid and that of hydrochloric acid consumed at the time of feeding. Further, the quantity of phosgene is sufficient to be 1.0 to 1.5 times its stoichiometrical quantity relative to the diamines, i.e. 1.0 to 1.5 times by mol the mols of the diamines.

A usual preferred embodiment of the process of the present invention is as follows:

Water and a diamine are added into a reactor equipped with a phosgene-blowing tube, a dropping funnel, an electrode for pH measurement, a thermometer, a reflux condenser and a stirrer. Hydrochloric acid is added to make the pH of the fed solution about 3 to 10, followed by introducing phosgene through the phosgene-blowing tube while agitating the solution at a suitable temperature, and at the same time dropwise adding a dehydrochlorinating agent through the dropping funnel, to thereby keep the pH of the reaction liquid at 3.0 to 10.0, preferably 5.0 to 8.0, purging unreacted phosgene by nitrogen gas after completion of the blowing and the dropwise addition, and taking out the objective product in a conventional manner such as extraction and/or distillation, etc.

The present invention will be described in more detail by way of Examples and Comparative examples.

EXAMPLE 1

Water (100 ml) and N,N'-dimethyl-1,2-propane-diamine (20.4 g, 0.20 mol) were placed in a 300 ml glass flask equipped with a phosgene-blowing tube, a dropping funnel, a thermometer, a reflux condenser and a stirrer, and on the other hand, 20% NaOH aqueous solution (84.0 g, 0.40 mol) was placed in the dropping funnel. Phosgene was blown in the flask through the phosgene-blowing tube with stirring at a rate of 10 g/hr. for 2 hours while the inner temperature of the flask was kept at 20° C. At the same time, 20% NaOH aqueous solution was dropwise added through the dropping funnel over 2 hours. After completion of the blowing and dropwise addition, aging was carried out at 20° C. for one hour. A sample was taken from the resulting reaction mass and the quantity of 1,3,4-trimethyl-2-imidazolidinone was determined according to gas chromatography. The production yield was 78.9%.

EXAMPLE 2

Reaction was carried out in the same manner as in Example 1 except that N,N'-dimethyl-1,2-propanediamine was replaced by N,N'-2-trimethyl-2,3-butanediamine (26.1 g, 0.20 mol), followed by analysis. As a result the production yield of 1,3,4,4,5- pentamethyl-2-imidazolidinone was 76.7%.

EXAMPLE 3

Reaction was carried out in the same manner as in Example 1 except that N,N'-dimethyl-1,2-propanediamine was replaced by N,N'-diethyl-1,2-propanediamine (26.1 g, 0.20 mol), followed by analysis. As a result the production yield of 1,3-diethyl-4- methyl-2-imidazolidinone was 77.3%.

EXAMPLE 4

Reaction was carried out in the same manner as in Example 1 except that 20% NaOH aqueous solution was replaced by triethylamine (40.5 g, 0.40 mol), followed by analysis. The production yield of 1,3,4-trimethyl-2-imidazolidinone was 71.4%.

EXAMPLE 5

Water (100 ml), N,N'-dimethyl-1,2-propanediamine (20.4 g, 0.20 mol) and 36% hydrochloric acid (30.4 g, 0.30 mol) were placed in a 500 ml glass flask equipped with a phosgene-blowing tube, a dropping funnel, an electrode for pH measurement, a thermometer, a reflux condenser and a stirrer.

On the other hand, 20% NaOH aqueous solution (168.0 g, 0.80 mol) was placed in the dropping funnel. Phosgene was blown in the flask with stirring at a rate of 10 g/hr. over 2 hours while the reaction temperature was kept at 20° C. under cooling. At the same time, 20% NaOH aqueous solution was dropwise added over 2 hours while the pH of the reaction liquid was controlled to 7.0±0.3.

After completion of the blowing and dropwise addition, the inside of the system was purged with nitrogen gas at a rate of 20 min. for 20 minutes.

A sample was taken from the resulting reaction mass and the quantity of 1,3,4-trimethyl-2-imidazolidinone was determined according to gas chromatography. The production yield was 91.3%. 49% NaOH aqueous solution was added to the reaction-completed liquid to make it alkaline, followed by twice extracting the resulting material with 1,2-dichloroethane (150 g/once), separating the resulting oil layer and distilling it to obtain 1,3,4-trimethyl-2-imidazolidinone (b.p. 133°–135° C./20 torr)(21.8 g).

COMPARATIVE EXAMPLE 1

Toluene (100 ml) and N,N'-dimethyl-1,2-propanediamine (20.4 g, 0.20 mol) were placed in a 300 ml glass flask equipped with a phosgene-blowing tube, a thermometer, a reflux condenser and a stirrer. Phosgene was blown in the flask through the phosgene-blowing tube with stirring at a rate of 10 g/hr. for 2 hours while the inner temperature of the flask was kept at 20° C., followed by aging the resulting material at the same temperature for one hour. A sample was taken from the resulting reaction mass and the quantity of 1,3,4-trimethyl-2-imidazolidinone was determined according to gas chromatography. The production yield was 18.3%.

EXAMPLE 6

Water (100 ml) and N,N'-dimethyl-1,3-propanediamine (20.4 g, 0.20 mol) were placed in a 300 ml glass flask equipped with a phosgene-blowing tube, a dropping funnel, a thermometer, a reflux condenser and a stirrer, and on the other hand, 20% NaOH aqueous solution (84.0 g, 0.4 mol) was placed in the dropping funnel.

Phosgene was blown in the flask through the phosgene-blowing tube with stirring at a rate of 10 g/hr. for 2 hours while the inner temperature of the flask was kept at 20° C. At the same time, 20% NaOH aqueous solution was dropwise added through the dropping funnel over 2 hours. After completion of the blowing and dropwise addition, the resulting material was aged at 20° C. for one hour.

A sample was taken from the resulting reaction mass and the quantity of tetrahydro-1,3-dimethyl-2(1H)-pyrimidinone was determined. The production yield was 77.1%.

EXAMPLE 7

Reaction was carried out in the same manner as in Example 6 except that N,N'-dimethyl-1,3-propanediamine was replaced by 1,3-propanediamine (14.8 g, 0.20 mol), followed by analysis. As a result, the production yield of tetrahydro-2(1H)-pyrimidinone was 76.8%.

EXAMPLE 8

Reaction was carried out in the same manner as in Example 6, except that N,N'-dimethyl-1,3-propanediamine was replaced by N,N'-diethyl-1,3-propanediamine (26.0 g, 0.20 mol), followed by analysis. As a result the production yield of 1,3-diethyltetra- hydro-2(1H)-pyrimidinone was 73.3%.

EXAMPLE 9

Reaction was carried out in the same manner as in Example 6 except that N,N'-dimethyl-1,3-propanediamine was replaced by N,N'-dibutyl-1,3-propanediamine (37.2 g, 0.20 mol), followed by analysis. As a result, the production yield of 1,3-dibutyl- tetrahydro-2(1H)-pyrimidinone was 71.9%.

EXAMPLE 10

Reaction was carried out in the same manner as in Example 6 except that N,N'-dimethyl-1,3-propanediamine was replaced by 2,2-dimethyl-1,3-propanediamine (20.4 g, 0.20 mol), followed by analysis. As a result, the production yield of tetrahydro-5,5- dimethyl-2(1H)-pyrimidinone was 75.5%.

EXAMPLE 11

Reaction was carried out in the same manner as in Example 6 except that N,N'-dimethyl-1,3-propanediamine was replaced by N,N',2,2-tetramethyl-1,3-propanediamine (26.0 g, 0.20 mol). As a result, the production yield of tetrahydro-1,3,5,5-tetramethyl-2(1H)-pyrimidinone was 73.9%.

EXAMPLE 12

Reaction was carried out in the same manner as in Example 6 except that 20% NaOH aqueous solution was replaced by triethylamine (40.5 g, 0.40 mol), followed by analysis. As a result, the production yield of tetrahydro-1,3-dimethyl-2(1H)-pyrmidinone was 70.4%.

EXAMPLE 13

Water (100 ml), N,N'-dimethyl-1,3-propanediamine (20.4 g, 0.20 mol) and 36% hydrochloric acid (30.4 g, 0.30 mol) were placed in a 500 ml flask equipped with a phosgene-blowing tube, a dropping funnel, an electrode for pH measurement, a thermometer, a reflux condenser and a stirrer. On the other hand, 20% NaOH aqueous solution (168.0 g, 0.80 mol) was placed in the dropping funnel.

Phosgene was blown in the flask through the phosgene-blowing tube with stirring at a rate of 10 g/hr. for 2 hours while the reaction temperature was kept at 20° C. under cooling. At the same time, 20% NaOH aqueous solution was dropwise added over 2 hours while the pH of the reaction liquid was controlled to 7.0 ±0.3. After completion of the blowing and dropwise addition, the inside of the system was purged with nitrogen gas at a rate of 20 l/min. for 20 minutes.

A sample was taken from the resulting reaction mass and the quantity of tetrahydro-1,3-dimethyl-2(1H)-pyrimidinone was determined according to gas chromatography. The production yield was 90.7%. 40% NaOH aqueous solution was added to the reaction-completed liquid to make the pH value in the vicinity of 12, followed by twice extracting the resulting material with 1,2-dichloroethane (150 g/once), separating the resulting oil layer and distilling it to obtain tetrahydro-1,3-dimethyl-2(1H)-pyrimidinone (a fraction of b.p. 93–94° C./5 torr)(21.8 g).

COMPARATIVE EXAMPLE 2

Toluene (100 ml) and N,N'-dimethyl-1,3-propanediamine (20.4 g, 0.20 mol) were placed in a 300 ml glass flask equipped with a phosgene-blowing tube, a thermometer, a reflux condenser and a stirrer. Phosgene was blown in the flask through the phosgene-blowing tube with stirring ate of 10 g/hr. for 2 hours while the inner temperature of the flask was kept at 20° C.

A sample was taken from the resulting reaction mass and the quantity of tetrahydro-1,3-dimethyl-2(1H)-pyrimidinone was determined. The production yield was 17.6%.

EXAMPLE 14

Water (100 ml) and N,N'-dimethyl-1,4-butanediamine (23.2) g, 0.20 mol) were placed in a 300 ml glass flask equipped with a phosgene-blowing tube, a dropping funnel, a thermometer, a reflux condenser and a stirrer, and on the other hand, 20% NaOH aqueous solution (84.0 g, 0.40 mol) was placed in the dropping funnel. Phosgene was blown in the flask through the phosgene-blowing tube with stirring at a rate of 10 g/hr. for 2 hours while the inner temperature of the flask was kept at 20° C. At the same time, 20% NaOH aqueous solution was dropwise added through the dropping funnel over 2 hours. After completion of the blowing and dropwise addition, the resulting material was aged at 20° C. for one hour. A sample was taken from the resulting reaction mass and the quantity of hexahydro-1,3-dimethyl-2H-1,3-diazepin-2-one was determined. The production yield was 78.9%.

EXAMPLE 15

Reaction was carried out in the same manner as in Example 14 except that N,N'-dimethyl-1,4-butanediamine was replaced by 1,4-butanediamine (17.6 g, 0.20 mol), followed by analysis. As a result, the production yield of hexahydro-2H-1,3-diazepin-2-one was 80.1%.

EXAMPLE 16

Reaction was carried out in the same manner as in Example 14, except that N,N'-dimethyl-1,4-butanediamine was replaced by N,N'-diethyl-1,4-butanediamine (28.9 g, 0.20 mol), followed by analysis. As a result, the production yield of 1,3-diethyl- hexahydro-2H-1,3-diazepin-2-one was 75.7%.

EXAMPLE 17

Reaction was carried out in the same manner as in Example 14, except that N,N'-dimethyl-1,4-butanediamine was replaced by N,N'-dipropyl-1,4-butanediamine (31.7 g, 0.20 mol), followed by analysis. As a result, the production yield of hexahydro-1,3-dipropyl-2H,3-diazepin-2-one was 72.7%.

EXAMPLE 18

Reaction was carried out in the same manner as in Example 14 except that N,N'-dimethyl-1,4-butanediamine was replaced by N,N'-dibutyl-1,4-butanediamine (34.5 g, 0.20 mol). As a result, the production yield of 1,3-dibutyl-hexahydro-2H-1,3-diazepin-2-one was 72.3%.

EXAMPLE 19

Reaction was carried out in the same manner as in Example 14 except that N,N'-dimethyl-1,4-butanediamine was replaced by 2,5-dimethyl-2,5-hexanediamine (28.9 g, 0.20 mol), followed by analysis. As a result, the production yield of hexahydro-2H-4,4,7,7-tetramethyl-2H-1,3-diazepine-2-one was 75.2%.

EXAMPLE 20

Reaction was carried out in the same manner as in Example 14, except that 20% NaOH aqueous solution was replaced by triethylamine (40.5 g, 0.40 mol), followed by analysis. As a result, the production yield of hexahydro-1,3-dimethyl-2H-1,3-diazepin-2-one was 71.4%.

EXAMPLE 21

Water (100 ml), N,N'-dimethyl-1-4-butanediamine (23.2 g, 0.20 mol) and 36% hydrochloric acid (30.4 g, 0.30 mol) were placed in a 500 ml glass flask equipped with a phosgene-blowing tube, a dropping funnel, an electrode for pH measurement, a thermometer, a reflux condenser and a stirrer.

On the other hand, 20% NaOH aqueous solution (168.0 g, 0.80 mol) was placed in the dropping funnel. Phosgene was blown in the flask with stirring at a rate of 10 g/hr. over 2 hours while the reaction temperature was kept at 20° C. under cooling. At the same time, 20% NaOH aqueous solution was dropwise added over 2 hours while the pH of the reaction liquid was controlled to 7.0±0.3. After completion of the blowing and dropwise addition, the inside of the system was purged with nitrogen gas at a rate of 20 l/min. for 20 minutes.

A sample was taken from the resulting reaction mass and the quantity of hexahydro-1,3-dimethyl-2H-1,3-diazepin-2-one was determined according to gas chromatography. The production yield was 91.2%. 49% NaOH aqueous solution was added to the reaction-completed liquid to make the pH a value in the vicinity of 12, followed by twice extracting the resulting material with 1,2-dichloroethane (150 g/once), separating the resulting oil layer and distilling it to obtain hexahydro-1,3-dimethyl-2H-1,3-diazepin-2-one (a fraction of b.p. 94–95° C./4 torr) (24.1 g).

COMPARATIVE EXAMPLE 3

Toluene (100 ml) and N,N'-dimethyl-1,4-butanediamine (23.2 g, 0.20 mol) were placed in a 300 ml glass flask equipped with a phosgene-blowing tube, a thermometer, a reflux condenser and a stirrer. Phosgene was blown in the flask through the phosgene-blowing tube with stirring a rate of 10 g/hr. for 2 hours while the inner temperature of the flask was kept at 20° C.

A sample was taken from the resulting reaction mass and the quantity of hexahydro-1,3-dimethyl-2H-1,3-diazepin-2-one was determined according to gas chromatography. The production yield was 15.3%.

EXAMPLE 22

Water (100 ml) and N,N'-diethyl-ethylenediamine (11.6 g, 0.1 mol) were placed in a 300 ml 4-neck-flask equipped with a reflux condenser, a thermometer, a dropping funnel, a phosgene-blowing tube and a stirrer, and on the other hand, triethylamine (20.2 g, 0.2 mol) was placed in the dropping funnel. Phosgene was blown in the flask through the phosgene-blowing tube with stirring at a rate of 10 g/hr. for one hour while the flask was kept at 20° C. At the same time, triethylamine was dropwise added through the dropping funnel over one hour. After completion of the blowing and dropwise addition, the resulting material was aged at 20° C. for one hour. A sample was taken out from the reaction mass and the quantity of 1,3-diethyl-2-imidazolidinone was determined. The theoretical yield was 76.6%.

EXAMPLE 23

Water (100 ml), N,N'-diethylethylenediamine (23.2 g, 0.2 mol) and 36% hydrochloric acid (30.4 g, 0.3 mol) were placed in a 500 ml flask equipped with a reflux condenser, a thermometer, a dropping funnel, a phosgene-blowing tube, an electrode for pH measurement and a stirrer. On the other hand, 20% NaOH aqueous solution (168.0 g, 0.8 mol) was placed in the dropping funnel. Phosgene was blown in the flask with stirring at a rate of 10 g/hr. for 2 hours while the reaction temperature was kept at 20° C. under cooling. At the same time, 20% NaOH aqueous solution was dropwise added over 2 hours while the pH of the reaction liquid was controlled to 7.0±0.3. After completion of the blowing and dropwise addition, the inside of the system was purged with nitrogen gas at a rate of 20 l/min. A sample was taken out from the reaction mass and the quantity of 1,3-diethyl-2-imidazolidinone was determined. As a result, unreacted N,N'-diethylenediamine (1.2 g, conversion 94.8 g) and 1,3-diethyl-2-imidazolidinone (25.6 g, selectivity 95.2%) were present.

48% NaOH aqueous solutionw as added to the reaction-completed liquid to make the pH a value in the vicinity of 10, followed by twice extracting the resulting material with 1,2-dichloroethane (150 g/once), separating the resulting oil layer and distilling it to obtain 1,3,diethyl-2-imidazolidinone (a fraction of b.p. 146–149° C./20–25 mm Hg) (24.5 g).

EXAMPLE 24

Reaction was carried out in the same manner as in Example 22 except that N,N'-diethylethylenediamine was replaced by N,N'-dipropylethylenediamine (14.4 g, 0.1 mol) followed by analysis. As a result, 1,3-dipropyl- 2-imidazolidinone was formed with a theoretical yield of 70.0%.

What is claimed is:

1. In a process for producing a cyclic urea which comprises reacting a diamine expressed by the formula (II)

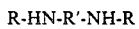 (II)

wherein R represents hydrogen atom or a lower alkyl group and R' represents dimethylene group, a lower alkyl group-substituted dimethylene group, trimethylene group, a lower alkyl group-substituted trimethylene group, tetramethylene group, a lower alkyl group-substituted tetramethylene group, but a case where R represents hydrogen atom and R' represents dimethylene group, a case where R represents hydrogen atom and R' represents a lower alkyl group-substituted dimethylene group and a case where R represents methyl group and R' represents dimethylene group are excluded, with phosgene in the presence of a dehydrochlorinating agent, the improvement which comprises at first converting said diamine to its hydrochloride and thereafter, reacting the hydrochloride with phosgene in a molar ration of 1.0 to 1.5 of phosgene to diamine in water solvent while maintaining a pH of the reaction liquid in the range of 5.0 to 8.0 by said dehydrochlorinating agent to obtain a cyclic urea expressed in the formula (I)

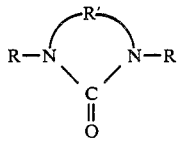 (I)

wherein R and R' are each as defined above.

* * * * *